United States Patent [19]

Findeisen et al.

[11] 4,328,351

[45] May 4, 1982

[54] PREPARATION OF TRIMETHYLSILYL CYANIDE

[75] Inventors: Kurt Findeisen, Odenthal; Karl-Heinz Linker, Leverkusen, both of Fed. Rep. of Germany

[73] Assignee: Bayer Aktiengesellschaft, Leverkusen, Fed. Rep. of Germany

[21] Appl. No.: 256,763

[22] Filed: Apr. 23, 1981

[30] Foreign Application Priority Data

May 16, 1980 [DE] Fed. Rep. of Germany ....... 3018821

[51] Int. Cl.$^3$ ................................................ C07F 7/10
[52] U.S. Cl. ................................................ 556/415
[58] Field of Search ........................................ 556/415

[56] References Cited

U.S. PATENT DOCUMENTS 3,032,575  5/1962  Freitag et al. ..................... 556/415

OTHER PUBLICATIONS

"J.A.C.S.", 80, 8/58, pp. 4151–4153.

Noll, "Chemistry and Technology of Silicones", Academic Press, N.Y. (1968), p. 113.

*Primary Examiner*—Paul F. Shaver
*Attorney, Agent, or Firm*—Sprung, Felfe, Horn, Lynch & Kramer

[57] ABSTRACT

A process for the preparation of trimethylsilyl cyanide comprising reacting trimethylsilyl chloride with an approximately equimolar amount of an alkali metal cyanide in the presence of a catalytic amount of a heavy metal cyanide and in the presence of an aprotic solvent with a boiling point above about 150° C., at a temperature between about 130° and 250° C. Advantageously the reaction temperature is between about 160° and 220° C., the alkali metal cyanide is sodium cyanide or potassium cyanide, the heavy metal cyanide is copper(I) cyanide, copper(II) cyanide, zinc cyanide or a complex compound of one of them with an alkali metal cyanide and is employed in about 1 to 8 mol % relative to the alkali metal cyanide, and the mixture of aprotic solvent, heavy metal cyanide and alkali metal chloride remaining in the reaction vessel when the reaction has ended is used directly as the reaction medium for a further batch.

11 Claims, No Drawings

PREPARATION OF TRIMETHYLSILYL CYANIDE

The present invention relates to an unobvious process for the preparation of trimethylsilyl cyanide from trimethylsilyl chloride.

Trimethylsilyl cyanide is a valuable intermediate product, inter alia for the preparation of acyl cyanides, and can thus be used, for example, for the synthesis of certain herbicidally active heterocyclic compounds.

A number of processes for the preparation of trimethylsilyl cyanide are described in the literature, but these all have disadvantages to a greater or lesser extent. The trimethylsilyl cyanide is prpared either using silver cyanide (J. Amer. Chem. Soc. 81,4493 (1959)), which is expensive, or hydrogen cyanide (J. Org. Chem. 39, 914 (1974): Synthesis 1978, 154; and J. Amer. Chem. Soc. 80, 4151 (1958)), which is relatively difficult to handle on an industrial scale. Other processes require a high expenditure on apparatus (Z. Anorg. Allg. Chem. 313, 290 (1962); Tetrahedron Letters 1975, 71; and J. Org. Chem. 43, 2280 (1978)).

A synthesis using trimethylsilyl chloride and excess sodium cyanide or potassium cyanide in N-methyl-pyrrolidone as a solvent has recently been disclosed (S. Hünig et al., Synthesis 1979, 522 and J. K. Rasmussen et al., Synthesis 1979, 523). According to Rasmussen et al., the yield for a 0.4 mol batch using potassium cyanide is 71% of theory. According to Hünig et al., the phase-transfer catalyst Adogen 464 (see Angew. Chem. 90, 58 (1978)) must be added in the case of a 5 mol batch, using sodium cyanide, in order to achieve a yield of 60 to 70% of theory, since the yields are otherwise only 20 to 30% of theory.

Apart from the moderate yield, both process variants have the disadvantage that the alkali metal cyanide must be employed in excess and that relatively long reaction times are required; thus, a reaction time of 30 to 36 hours is required for the reaction of 5 mols of trimethylsilyl chloride with sodium cyanide and a reaction time of 16 hours is required for the reaction of 0.4 mol of trimethylsilyl chloride with potassium cyanide. In addition, as stated, a certain phase-transfer catalyst must be added in the case of one of the two process variants.

There was thus an urgent industrial need for the processes known hitherto, starting from trimethylsilyl chloride and alkali metal cyanide, to be improved to such an extent that the reaction times are reduced to an industrially acceptable level, the use of excesses of alkali metal cyanide is avoided and the yields in industrial batches are also considerably increased.

The present invention now provides a process for the preparation of trimethylsilyl cyanide, in which trimethylsilyl chloride is reacted with approximately the equimolar amount of an alkali metal cyanide in the presence of a catalytic amount of a heavy metal cyanide and in the presence of an aprotic solvent with a boiling point above about 150° C., at a temperature between about 130° and 250° C., and the trimethylsilyl cyanide is removed from the reaction mixture, by distillation, at the rate at which it is formed, any unreacted trimethylsilyl chloride also distilled at the same time being separated off from the trimethylsilyl cyanide by evaporation and being recycled back into the reaction vessel until virtually all of it has reacted.

Surprisingly, by means of the present invention, trimethylsilyl cyanide can be obtained from trimethylsilyl chloride and an alkali metal cyanide in a very high yield and purity.

The process according to the invention avoids the disadvantages of the processes already known and thus represents a considerable improvement. Thus, the reaction time for a 4 mol batch, for example, is only about 2 hours. Only stoichiometric amounts of the alkali metal cyanide need to be employed, and the yields of pure trimethylsilyl cyanide are above 90% of theory.

If sodium cyanide is used as the alkali metal cyanide, copper(I) cyanide is used as the heavy metal cyanide and tetramethylene sulphone ("sulpholane") is used as the aprotic solvent, the course of the reaction can be represented by the following equation:

Sodium cyanide or potassium cyanide is preferably used as the alkali metal cyanide.

As heavy metal cyanides which are employed in catalytic amounts there may be mentioned, as preferences, copper(I) cyanide, copper(II) cyanide and zinc cyanide, and complex compounds thereof with alkali metal cyanides, such as are formed, for example, in the reaction of sodium cyanide with copper(I) cyanide:

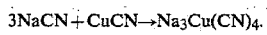

However, it is also possible to use heavy metal salts, which are converted into heavy metal cyanides under the reaction conditions.

Possible aprotic solvents which can be employed in carrying out the process according to the invention are any of the aprotic solvents which do not undergo a chemical reaction either with the trimethylsilyl chloride or with the metal cyanides and which have boiling points in a suitable boiling range (preferably 150° to 300° C.). Tetramethylene sulphone is the preferred solvent.

The reaction temperature can be varied within a substantial range; it should in all cases be higher than the boiling points of the trimethylsilyl chloride (about 57° C.) and the trimethylsilyl cyanide (about 117° C.). In general, the reaction is carried out, as stated above, at temperatures between 130° and 250° C., preferably between 160° and 220° C.

The reaction is in general carried out under normal pressure.

The trimethylsilyl chloride and alkali metal cyanide are preferably reacted in stoichiometric amounts in carrying out the process according to the invention. The heavy metal cyanide is employed in catalytic amounts, which are less than the stoichiometric amount, and in general in amounts of 0.5 to 10 mol %, preferably in amounts of 1 to 8 mol %, relative to the alkali metal cyanide.

The measure of removing the trimethylsilyl cyanide from the reaction mixture, by distillation, at the rate at which it is formed is furthermore of decisive importance for the success of the process according to the invention. Compared with the processes already known, this has the advantage that the reaction can be carried out at a higher temperature and hence with a substantially faster rate of reaction, and that, on the other hand, the very reactive trimethylsilyl cyanide formed in each case does not have to be heated in the reaction mixture for a long period; side reactions, which otherwise evidently occur and lead to significant losses in yield, are completely suppressed by this procedure.

In general, unreacted trimethylsilyl chloride is also distilled out of the reaction vessel, together with the trimethylsilyl cyanide, in an amount which largely depends on the rate at which it is fed in and on the chosen reaction temperature. In order to achieve complete conversion, it is expedient to separate off the relatively highly volatile trimethylsilyl chloride from the trimethylsilyl cyanide using a suitable apparatus (see Example 1), and to recycle it back into the reaction vessel until virtually complete conversion is achieved.

In a particular embodiment of the process according to the invention, the mixture of aprotic solvent, heavy metal cyanide and alkali metal chloride remaining in the reaction vessel when the reaction has ended can be used directly as the reaction medium for a further batch, under otherwise identical conditions. This reaction sequence can optionally be repeated several times, as long as the reaction medium can still easily be stirred. This embodiment is preferred and is a semi-continuous procedure.

Pure trimethylsilyl cyanide is obtained from the crude reaction product by subsequent distillation. The yields of pure trimethylsilyl cyanide are generally over 90% of theory.

Trimethylsilyl cyanide is a valuable intermediate product of organic chemistry which can be used in many ways (see, for example, Synthesis 1979, pages 522 and 523). In particular, it can be used as a starting material for the preparation of acyl cyanides (see, for example, Synthesis 1979, pages 204 to 205), which in turn can be employed for the synthesis of 1,2,4-triazin-5-ones, which have outstanding herbicidal properties.

Thus, for example, trimethylsilyl cyanide can be smoothly converted into pivaloyl cyanide by reaction with pivaloyl chloride, (CH$_3$)$_3$C—COCl+(CH$_3$)$_3$SiCN→(CH$_3$)$_3$C—COCN+(CH$_3$)$_3$SiCl, and the pivaloyl cyanide can be converted by known processes, for example into the herbicidally active compound 3-methylthio-4-amino-6-tert.-butyl-1,2,4-triazin-5(4H)-one (see, for example, German Pat. No. 1,795,784, DE-OS No. (German Offenlegungsschrift) 2,733,180, U.S. Pat. No. 4,175,188 and furthermore German Patent Applications Nos. P 30 02 203.8, P 30 03 541.7 and P 30 09 043.8).

Trimethylsilyl cyanide can be analogously converted into benzoyl cyanide by reaction with benzoyl chloride (see the preparative example given hereinafter), and the benzoyl cyanide can likewise be further reacted by known processes, for example to give the herbicidally active compound 3-methyl-4-amino-6-phenyl-1,2,4-triazin-5(4H)-one (see, for example, DE-OS'en (German Published Specifications) Nos. 2,224,161, 2,528,211, 2,708,189 and U.S. Pat. No. 3,959,372, filed 5/25/76.

The process of the present invention is illustrated in the following preparative example:

EXAMPLE 1

200 g (4 mol) of 98% pure sodium cyanide and 20 g (0.22 mol) of copper(I) cyanide in 500 ml of dry tetramethylene sulphone were initially introduced into a 2 liter four-necked flask (provided with a stirrer, thermometer and inlet tube, which was connected to a reservoir vessel for (CH$_3$)$_3$SiCl, and surmounted by a short column) and were heated to 180° to 190° C. 434 g (4 mol) of trimethylsilyl chloride (content, determined by gas chromatography: 98.6%) were allowed to run in slowly at this temperature. The trimethylsilyl cyanide formed in the course of the reaction was removed continuously from the reaction mixture by passing it, together with unreacted trimethylsilyl chloride, via the attached short column and a subsequent distillation bridge, out of the reaction vessel into a 1 liter four-necked flask (provided with a stirrer, thermometer and inlet tube from the abovementioned distillation bridge, surmounted by a column kept at 70° C. and provided with a bottom outlet valve) which was kept at 90° C. Because of its relatively low boiling point (about 57° C.), the trimethylsilyl chloride was driven out, by evaporation, of the mixture which had passed over and was recycled via the column kept at 70° C. and a subsequent distillation bridge into the reservoir vessel and was thus recycled back into the reaction vessel. After a reaction time of 2 hours, the given amount of trimethylsilyl chloride had reacted.

A further 200 g (4 mols) of sodium cyanide and 434 g (4 mols) of trimethylsilyl chloride were added to, or the latter was recycled into, the mobile tetramethylene sulphone/copper(I) cyanide/sodium cyanide suspension remaining in the reaction vessel. As described above, the reaction again took place at 180° to 190° C. in the course of 2 hours. The reaction medium which remained in the reaction vessel could still be easily stirred when the reaction had ended.

Another 200 g (4 mols) of sodium cyanide and 434 g (4 mols) of trimethylsilyl chloride were now added and were again reacted at 180° to 190° C. in the course of 2 hours, as described above.

The crude product drained off through the bottom outlet valve of the four-necked flask, which was kept at 90° C., still contained small amounts of trimethylsilyl chloride and, for separation and purification, was subjected to fractional distillation over a 30 cm long column with a column head. The residual trimethylsilyl chloride (boiling point: 57.3° C.) was first distilled off.

Trimethylsilyl cyanide (boiling point: 115° to 117° C.; melting point: about 15° C.) was obtained as the main fraction.

Total yield: 1,118 g of trimethylsilyl cyanide (=94% of theory).

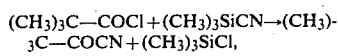
Reaction of trimethylsilyl cyanide ⟶

benzoyl cyanide (CH$_3$)$_3$SiCN + C$_6$H$_5$COCl ⟶

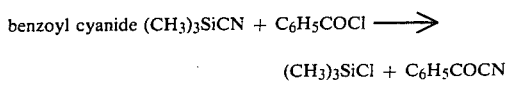
(CH$_3$)$_3$SiCl + C$_6$H$_5$COCN 70.3 g (0.5 mol) of benzoyl chloride were initially introduced into a 250 ml four-necked flask (provided with a stirrer, thermometer and dropping funnel and surmounted by a distillation bridge) and were warmed to 110° C. 49.5 g (0.5 mol) of trimethylsilyl cyanide were added dropwise in the course of 20 minutes; the trimethylsilyl chloride thereby formed was simultaneously distilled off. The residue was subjected to fractional distillation in vacuo.

Yield: 53 g (82% of theory) of benzoyl cyanide of boiling point 86° to 88° C./11 mbar and melting point 31° C.

It will be appreciated that the instant specification and examples are set forth by way of illustration and not limitation, and that various modifications and changes may be made without departing from the spirit and scope of the present invention.

We claim:

1. A process for the preparation of trimethylsilyl cyanide comprising reacting trimethylsilyl chloride with an approximately equimolar amount of an alkali metal cyanide in the presence of a catalytic amount of a heavy metal cyanide and in the presence of an aprotic solvent with a boiling point above about 150° C., at a temperature between about 130° and 250° C.

2. A process according to claim 1, including the further steps of distilling off trimethylsilyl cyanide from the reaction mixture during the course of the reaction at about the rate at which it is formed, distilling off from the distillate any unreacted trimethylsilyl chloride distilled over therewith, and recycling to the reaction mixture such trimethylsilyl chloride distillate.

3. A process according to claim 1, wherein the reaction temperature is between about 160° and 220° C.

4. A process according to claim 1, wherein the heavy metal cyanide is employed in about 0.5 to 10 mol % relative to the alkali metal cyanide.

5. A process according to claim 1, wherein the heavy metal cyanide is employed in about 1 to 8 mol % relative to the alkali metal cyanide.

6. A process according to claim 1, wherein the alkali metal cyanide is sodium cyanide or potassium cyanide.

7. A process according to claim 1, wherein the heavy metal cyanide is copper (I) cyanide, copper(II) cyanide, zinc cyanide or a complex compound of one of them with an alkali metal cyanide.

8. A process according to claim 1, wherein tetramethylene sulphone is employed as the aprotic solvent.

9. A process according to claim 1, wherein the heavy metal cyanide is formed in situ.

10. A process according to claim 1, wherein the mixture of aprotic solvent, heavy metal cyanide and alkali metal chloride remaining in the reaction vessel when the reaction has ended is used directly as the reaction medium for a further batch.

11. A process according to claim 2, wherein the reaction temperature is between about 160° and 220° C., the alkali metal cyanide is sodium cyanide or potassium cyanide, the heavy metal cyanide is copper(I) cyanide, copper(II) cyanide, zinc cyanide or a complex compound of one of them with an alkali metal cyanide and is employed in about 1 to 8 mol % relative to the alkali metal cyanide, and the mixture of aprotic solvent heavy metal cyanide and alkali metal chloride remaining in the reaction vessel when the reaction has ended is used directly as the reaction medium for a further batch.

* * * * *

UNITED STATES PATENT AND TRADEMARK OFFICE
CERTIFICATE OF CORRECTION

PATENT NO. : 4,238,351
DATED : December 9, 1980
INVENTOR(S) : Alfes et al

It is certified that error appears in the above-identified patent and that said Letters Patent are hereby corrected as shown below:

In the naming of the inventors, "Jacob" should read --Jakob--.

*Signed and Sealed this*

*Twenty-first* Day of *April 1981*

[SEAL]

Attest:

RENE D. TEGTMEYER

*Attesting Officer*    *Acting Commissioner of Patents and Trademarks*